(12) United States Patent
O'Reilly

(10) Patent No.: US 10,349,997 B1
(45) Date of Patent: Jul. 16, 2019

(54) CRYOGENIC TREATMENT SYSTEM

(71) Applicant: Lewis O'Reilly, Irvine, CA (US)

(72) Inventor: Lewis O'Reilly, Irvine, CA (US)

( * ) Notice: Subject to any disclaimer, the term of this patent is extended or adjusted under 35 U.S.C. 154(b) by 0 days.

(21) Appl. No.: 15/823,201

(22) Filed: Nov. 27, 2017

(51) Int. Cl.
| | |
|---|---|
| *A61B 18/02* | (2006.01) |
| *A61F 7/00* | (2006.01) |
| *F25D 3/10* | (2006.01) |
| *A61B 18/00* | (2006.01) |
| *B05B 12/08* | (2006.01) |

(52) U.S. Cl.
CPC ........ *A61B 18/0218* (2013.01); *A61F 7/0085* (2013.01); *F25D 3/107* (2013.01); *A61B 2018/00714* (2013.01); *B05B 12/08* (2013.01)

(58) Field of Classification Search
CPC ... A61B 18/02; A61B 18/0218; A61F 7/0085; F16C 7/02; F25D 3/10
USPC ...................................... 606/21–26
See application file for complete search history.

(56) References Cited

U.S. PATENT DOCUMENTS

| | | | |
|---|---|---|---|
| 4,280,499 A | 7/1981 | Sguazzi | |
| 5,814,040 A | 9/1998 | Nelson et al. | |
| 6,141,985 A | 11/2000 | Cluzeau et al. | |
| 6,226,996 B1 | 5/2001 | Weber et al. | |
| 6,960,202 B2 | 11/2005 | Cluzeau et al. | |
| 7,204,832 B2 | 4/2007 | Altshuler et al. | |
| 7,963,959 B2 | 6/2011 | Da Silva et al. | |
| 9,050,117 B2 | 6/2015 | Nelson et al. | |
| 9,101,743 B2 | 8/2015 | Bangera et al. | |
| 2008/0255505 A1* | 10/2008 | Carlson | A61M 25/0662 604/95.04 |
| 2010/0168726 A1 | 7/2010 | Brookman | |
| 2012/0226268 A1* | 9/2012 | Liu | A61B 18/203 606/9 |
| 2015/0126985 A1* | 5/2015 | Newell | A61B 18/02 606/21 |
| 2015/0351822 A1* | 12/2015 | Mulcahey | A61B 90/98 606/22 |

* cited by examiner

Primary Examiner — Michael F Peffley
Assistant Examiner — Khadijeh A Vahdat
(74) Attorney, Agent, or Firm — Eric Karich; Karich & Associates

(57) ABSTRACT

A cryogenic treatment system has a housing that includes a dispensing nozzle operably connected with a CO2 dispensing conduit that includes a valve for controlling the flow of CO2 therethrough. A connector fitting is adapted for operably connecting the CO2 dispensing conduit with the separate CO2 source, which is not mounted on the housing. A temperature sensor is operably mounted for monitoring the temperature of a treated area of the patient, and an accelerometer is operably mounted for monitoring movement of the housing. A computer controller is operably connected with the temperature sensor and the accelerometer for controlling the valve responsive to the temperature sensor and the accelerometer.

1 Claim, 3 Drawing Sheets

CRYOGENIC TREATMENT SYSTEM

BACKGROUND OF THE INVENTION

Field of the Invention

This invention relates generally to cryogenic treatment systems, and more particularly to a cryogenic treatment system used to treat a body of a living patient, human or animal, for pain reduction, inflammation reduction, stimulation of circulation, muscle relaxation, skin treatments, and related effects.

Description of Related Art

The prior art teaches various forms of cryogenic treatment system used to treat a body of a living patient, human or animal, for pain reduction, inflammation reduction, stimulation of circulation, muscle relaxation, skin treatments, and related effects. Compressed carbon dioxide ($CO_2$) is known to be useful in cryotherapy, quickly, effectively, and safely cooling the patient's skin to reduced temperatures that are effective in treating the patient for various problems.

Cluzeau, U.S. Pat. No. 6,141,985, teaches a self-contained and portable cryogenic apparatus that includes a canister of carbon dioxide mounted on the top of the apparatus. The carbon dioxide is dispensed from the apparatus for treating the patient for the various conditions noted above. Since the carbon dioxide canister is mounted on the top of the apparatus, and angled downwardly, only the liquid carbon dioxide is dispensed, providing superior performance, and avoiding problems associated with gaseous $CO_2$ interfering with the flow of the liquid $CO_2$. This reference is incorporated by reference in its entirety.

The prior art teaches a cryogenic treatment apparatus having a $CO_2$ canister mounted on top of the apparatus. However, the prior art does not teach a cryogenic treatment system having the features and benefits described below. The present invention fulfills these needs and provides further advantages as described in the following summary.

SUMMARY OF THE INVENTION

The present invention teaches certain benefits in construction and use which give rise to the objectives described below.

The present invention provides a cryogenic treatment system for dispensing carbon dioxide ($CO_2$) from a separate $CO_2$ source for the treatment of a patient. The cryogenic treatment system includes a housing having a proximal end and a distal end; a dispensing nozzle operably mounted on the proximal end of the housing; a $CO_2$ dispensing conduit that includes a valve for controlling the flow of $CO_2$ through the $CO_2$ dispensing conduit to the dispensing nozzle; a connector fitting mounted on the housing and adapted for operably connecting the $CO_2$ dispensing conduit with the separate $CO_2$ source; a temperature sensor operably mounted on the housing adjacent the dispensing nozzle; an accelerometer operably mounted on or within the housing; and a computer controller operably connected with the temperature sensor and the accelerometer for controlling the valve responsive to the temperature sensor and the accelerometer.

A primary objective of the present invention is to provide a cryogenic treatment system having advantages not taught by the prior art.

Another objective is to provide a cryogenic treatment system that provides increased safety for the patient.

A further objective is to provide a cryogenic treatment system that is able to automatically halt the flow of $CO_2$ in the event that certain monitored conditions exceed acceptable parameters.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

The above-described drawing figures illustrate the invention, a cryogenic treatment system 10 used to treat a body of a living patient 12, human or animal, for pain reduction, inflammation reduction, stimulation of circulation, muscle relaxation, skin treatments, and other known forms of treatments.

Figure 1:
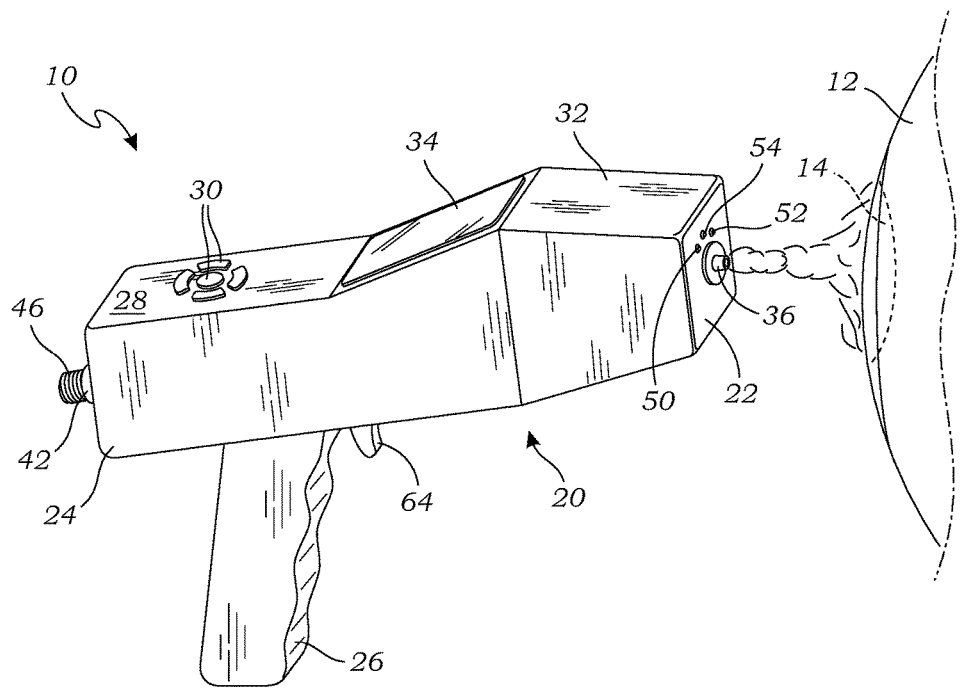
FIG. 1 is a perspective view of one embodiment of a cryogenic treatment system that embodies the present invention.
Figure 2:
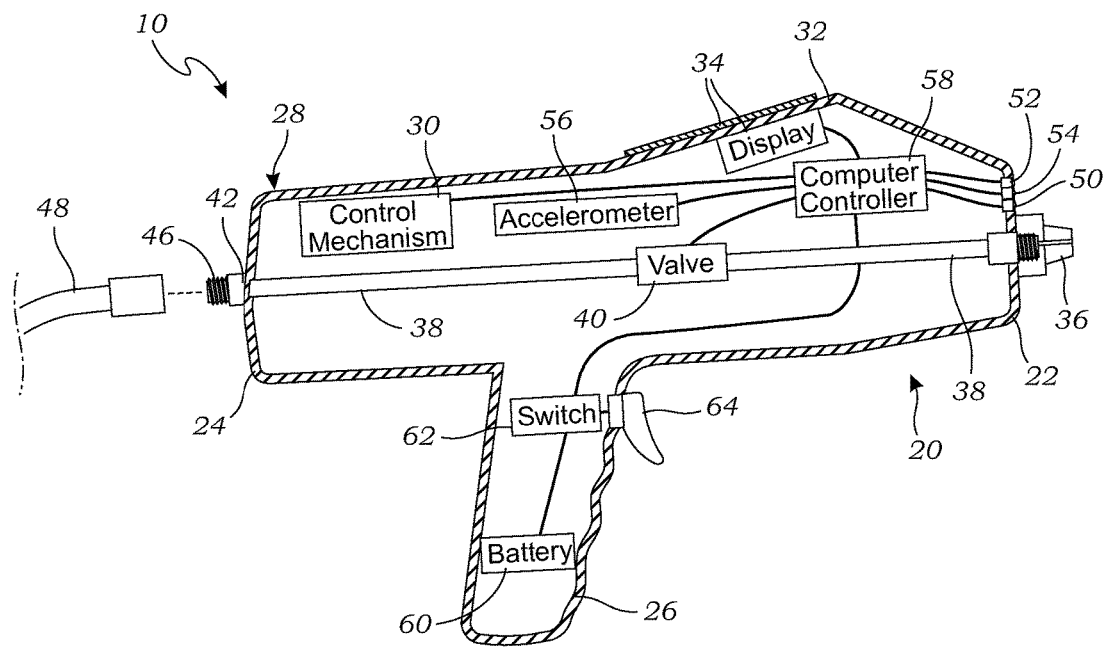
FIG. 2 is a side cross sectional view thereof.

FIG. 1 is a perspective view of one embodiment of a cryogenic treatment system 10 that embodies the present invention. FIG. 2 is a side cross sectional view thereof. As shown in FIGS. 1 and 2, the cryogenic treatment system 10 is adapted for dispensing carbon dioxide ($CO_2$) from a $CO_2$ source 70 for the therapeutic treatment of a patient 12. In the embodiment of FIGS. 1 and 2, the cryogenic treatment system 10 comprises a housing 20 having a proximal end 22 and a distal end 24. The housing 20 in this embodiment is in the form of a gun, and includes a handle 26 for facilitating use of the system. The housing 20 further includes a top surface 28 that may include a control mechanism 30 (e.g., buttons, switches, touch screen, etc.) for controlling the operation of the system. The top surface 28 may further include an angled display frame 32 for mounting a display 34 such that the display 34 is at an angle to the rest of the top surface 28, which is typically parallel to an axis of the housing 20. Mounting the display 34 at an angle (typically, for example, about 30-45 degrees) facilitates viewing the display 34 during treatment. For purposes of this application, the term "about" is defined to mean+/−10%).

As shown in FIGS. 1 and 2, a dispensing nozzle 36 is operably mounted on the proximal end 22 of the housing 20, typically aligned so that the dispensing nozzle 36 dispenses the $CO_2$ along the axis of the housing 20. In this embodiment, the dispensing nozzle 36 is removably mounted (e.g., threadedly, or via an equivalent structure known in the art) so that different nozzles may be used to achieve a desired treatment. In alternative embodiments, the nozzle 36 may be fixedly mounted, or mounted in some other manner. While one embodiment of the nozzle 36 is illustrated, alternative forms of nozzles and other forms of dispensing elements may also be used, and should be considered within the scope of the present invention.

As shown in FIG. 2, the dispensing nozzle 36 is operably connected to a CO2 dispensing conduit 38 that includes a valve 40 for controlling the flow of CO2 through the CO2 dispensing conduit 38 to the dispensing nozzle 36. In this embodiment, simply tubes are used, although alternative structures may also be used. In this embodiment, the valve 40 may be a solenoid valve, although any other suitable form of valve or control system known in the art may also be used. While one embodiment of the CO2 dispensing conduit 38 is illustrated, those skilled in the art may devise a wide range of alternative systems for controlling and directing the flow of CO2 through the system, and these alternative systems should be considered within the scope of the present invention.

Figure 3:
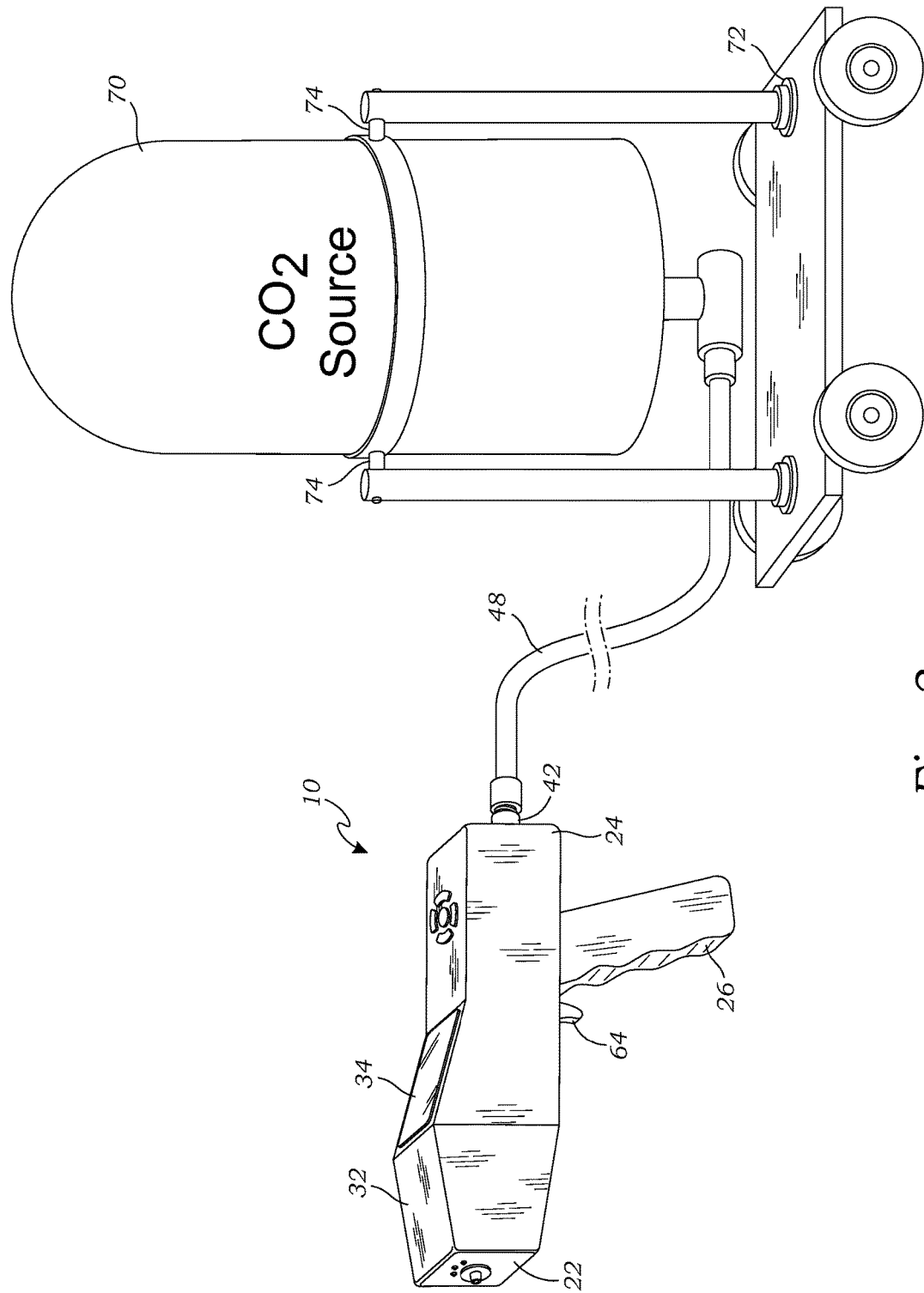
FIG. 3 is a perspective view of the cryogenic treatment system attached to a $CO_2$ source.

As shown in FIGS. 1 and 2, a connector fitting 42 may be mounted on the housing 20 and adapted for operably connecting the CO2 dispensing conduit 38 with the separate CO2 source 70. In this embodiment, the connector fitting 42 is mounted on the distal end 24 of the housing 20, opposite the dispensing nozzle 36; however, it may alternately be mounted in other locations. The connector fitting 42 in this embodiment includes a threaded connection 46 that enables an external hose 48 to be threadedly connected to the housing 20, although other connections known in the art are also acceptable, and within the scope of the present invention. It is preferred that the connection enable the hose to be connected and disconnected quickly and easily, and preferably without requiring the use of tools; however, this is not required, and more permanent connections may also be used. One embodiment of the CO2 source 70 is shown in FIG. 3 and discussed below; however, in alternative embodiments, alternative forms of CO2 sources 70 may be used, and should be considered within the scope of the present invention.

As shown in FIGS. 1 and 2, a range finder 50 may be operably mounted on the housing 20 adjacent the dispensing nozzle 36, for determining a distance from the nozzle 36 to the patient 12. The range finder 50 may be in the form of a laser, although other electronic methods (e.g., radar, ultrasonic, etc.) of determining distance may also be used, and should be considered within the scope of the present invention. The range finder 50 is useful for guiding the operator of the system 10 to position the system 10 the correct distance from the patient 12, not getting too close and causing harm, and potentially also guiding the operator to not be too far away so that the system 10 is not effective. For purposes of this application, the term "adjacent" is defined to include not only positions immediately adjoining, but also any position that is generally nearby, and operably positioned for use as described above.

As shown in FIGS. 1 and 2, a temperature sensor 52 may also operably mounted on the housing 20 adjacent the dispensing nozzle 36. The temperature sensor 52 may be any suitable sensor device, e.g., infrared pyrometer, or other equivalent device known in the art. The thermal sensor 52 is operably positioned to measure the temperature of the patient 12 in the treated area 14 (i.e., in front of the nozzle 36). The system 10 may further include an indicator light 54 that is illuminated when the treated area 14 is within a predetermined range of temperatures that are optimal for the treatment. The treatment is typically continued until the light 54 comes on, indicating a suitable temperature has been reached, and then the operator expands the treatment area into adjoining areas, until all of the target area is cooled to the correct temperature.

As shown in FIG. 2, an accelerometer 56 may also be included and operably mounted within or otherwise associated with the housing 20 for tracking movement of the system 10. This is important because proper movement of the system 10 by the operator is helpful in correctly treating the patient 12, and also avoiding potential injury to the patient 12. When used correctly, the system 10 is constantly in motion, preferably a circular movement that cools the target area without getting a single location so cold that injury is caused. Improper movement may result in feedback to the operator (e.g., alerts, audible instructions, etc.) instructing him or her to move the system 10 properly. It may also result in forced movement of the system 10, and/or turning off the system 10 to prevent injury, as discussed in greater detail below.

As shown in FIG. 2, a computer controller 58 may be mounted within the housing 20 and is operably connected with the various electronics (e.g., the range finder 50, the temperature sensor 52, the accelerometer 56, and any other sensors or components) for controlling the operation of the system 10, and in particular for controlling the valve 40 responsive to the range finder 50, the temperature sensor 52, and the accelerometer 56. The computer controller 58 may be in the form of any suitable computational device and/or system of devices. The computer controller 58 may be in the form of a microcontroller or other suitable electronics, and may include at least one computer processing element, e.g., circuitry, microcontroller, central processing unit (CPU), and/or any form of equivalent mechanism, and some form of computer memory having a capability to store data and/or instructions. The term "computer memory" as used herein refers to any tangible, non-transitory storage that participates in providing instructions to a processor for execution. Such a medium may take many forms, including but not limited to, non-volatile media, volatile media, and/or any equivalent media known in the art. Since these components are well known in the art, and a wide range of options may be used, these terms should be construed broadly to include any suitable electronics and/or computer components that are deemed suitable by those skilled in the art.

Also shown in FIG. 2, the system 10 may further include a battery 60 (e.g., a rechargeable battery with suitable recharging capabilities, typically replaceable batteries, etc.) and/or a port for connection with an external power supply (not shown). A switch 62 may be actuated by a trigger 64 for dispensing the CO2. Any suitable form of switch 62 or other triggering mechanism 64 may be used for this purpose, and in some embodiments a second "safety" switch 62 (not shown) may also be included, to prevent accidental discharge.

FIG. 3 is a perspective view of the system 10 attached to a CO2 source 70 such as a tank of liquid CO2. The CO2 source 70 may be physically separated from the housing 20 and operably connected with a hose or similar flexible connector. In this embodiment, the system 10 further includes a wheeled conveyance 72 for holding the tank and facilitating movement of the system 10. In this embodiment, the tank 70 is mounted on the conveyance 72 via pivots 74 so that the tank 70 may be readily flipped upside down. In this manner, the tank 70 is installed, and then can be inverted so that only the liquid component of the CO2 is dispensed, without gasses interfering with the dispensing process.

Figure 4:
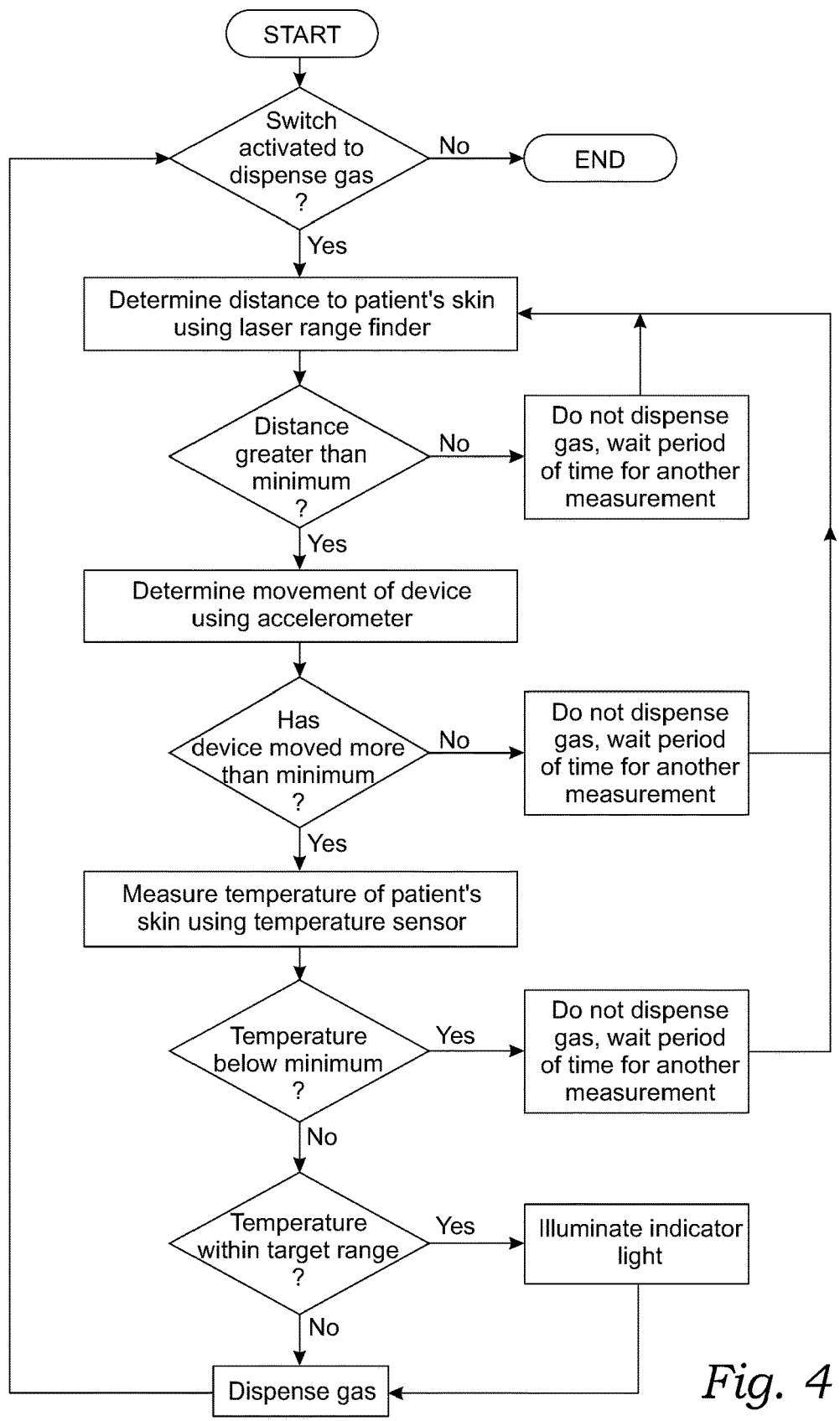
FIG. 4 is a flow diagram illustrating the operation of the cryogenic treatment system.

FIG. 4 is a flow diagram illustrating the operation of the cryogenic treatment system 10 of FIGS. 1 and 2. As shown in FIGS. 1-4, the computer controller 58 and the various sensors 50 and 52 shown in FIG. 2 performs many important functions to prevent injury to the patient 12, via the sensors discussed above. A distance from the dispensing nozzle 36 to the patient 12 is determined via the range finder 50. A temperature of a treated area 14 of the patient 12 is also determined via the thermal sensor 52. Movement of the housing 20 via the accelerometer 56 is also monitored. The computer controller 58 then operates to stop the flow of CO2 through the valve 40 if any of the noted characteristics are outside of predetermined ranges of values. For example, if the patient 12 is closer than a minimum distance from the dispensing nozzle 36, or if the treated area 14 of the patient 12 is colder than a predetermined minimum temperature, or if the housing 20 has remained stationary for more than a predetermined period of time, the flow of CO2 is halted.

Those skilled in the art may obviously modify these processes to meet various goals. For example, lights, alerts, and audible instructions may obviously be used to guide the operator of the system 10, and to help prevent any treatment parameters from being violated. Only when treatment deviates beyond a certain point is the flow of CO2 automatically halted. Flow may be resumed immediately once the situation has been resolved, or, alternatively, it may operate as a "circuit breaker" and require further action to resume treatment. If certain problems persist, an alert may be generated indicating that the operator may require further training.

As used in this application, the words "a," "an," and "one" are defined to include one or more of the referenced item unless specifically stated otherwise. The terms "approximately" and "about" are defined to mean+/−10%, unless otherwise stated. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application. While the invention has been described with reference to at least one particular embodiment, it is to be clearly understood that the invention is not limited to these embodiments, but rather the scope of the invention is defined by the following claims.

What is claimed is:

1. A cryogenic treatment system for dispensing carbon dioxide (CO2) from a separate CO2 source for treatment of a patient, the cryogenic treatment system comprising:
   a housing having a proximal end and a distal end;
   a dispensing nozzle operably mounted on the proximal end of the housing;
   a CO2 dispensing conduit including a valve for controlling flow of CO2 through the CO2 dispensing conduit to the dispensing nozzle;
   a connector fitting mounted on the housing and adapted for operably connecting the CO2 dispensing conduit with the separate CO2 source;
   a temperature sensor operably mounted on the housing adjacent the dispensing nozzle;
   an accelerometer operably mounted within the housing;
   a computer controller operably connected with the temperature sensor and the accelerometer for controlling the valve of the CO2 dispensing conduit being responsive to the temperature sensor and the accelerometer
   further comprising a range finder operably mounted on the housing adjacent the dispensing nozzle for determining a distance from the dispensing nozzle to the patient;
   wherein the computer controller is operably connected to the range finder, and wherein the computer controller functions to close the valve of the CO2 dispensing conduit to halt further flow of CO2 in an event that the distance from the dispensing nozzle to the patient becomes too short.

* * * * *